United States Patent
Schäckel (10) Patent No.: US 7,154,604 B2
(45) Date of Patent: Dec. 26, 2006

(54) METHOD AND DEVICE FOR EVALUATING ELECTROMAGNETIC RADIATION

(75) Inventor: Ralf Schäckel, Everode (DE)

(73) Assignee: Fagus-Grecon Greten GmbH & Co. KG, Alfeld (DE)

(*) Notice: Subject to any disclaimer, the term of this patent is extended or adjusted under 35 U.S.C. 154(b) by 464 days.

(21) Appl. No.: 10/484,543

(22) PCT Filed: Jul. 16, 2002

(86) PCT No.: PCT/EP02/07901

§ 371 (c)(1),
(2), (4) Date: Jan. 22, 2004

(87) PCT Pub. No.: WO03/012381

PCT Pub. Date: Feb. 13, 2003

(65) Prior Publication Data

US 2004/0252305 A1    Dec. 16, 2004

(30) Foreign Application Priority Data

Jul. 21, 2001    (DE)  ................................ 101 35 705

(51) Int. Cl.
*G01N 21/00* (2006.01)
(52) U.S. Cl. ...................................................... 356/432
(58) Field of Classification Search ......... 356/432–440
See application file for complete search history.

(56) References Cited

U.S. PATENT DOCUMENTS

| 4,365,896 A | 12/1982 | Mihalow | 356/446 |
| 4,546,246 A | 10/1985 | Bechtel | 250/221 |
| 6,315,955 B1* | 11/2001 | Klein | 422/73 |

FOREIGN PATENT DOCUMENTS

| DE | 195 31 917 C1 | 3/1997 |
| DE | 199 51 403 A1 | 5/2001 |
| EP | 0 472 321 A1 | 2/1992 |

* cited by examiner

Primary Examiner—Gregory J. Toatley, Jr.
Assistant Examiner—Amanda Merlino
(74) Attorney, Agent, or Firm—Synnestvedt & Lechner LLP (57) ABSTRACT

A device is disclosed which detects and evaluates electromagnetic radiation from an area or region. The device includes two measuring chains, and a control and evaluation unit. Each measuring chain has a head forming a boundary surface for the area and is provided with a transmitter and a receiver. In order to test the device, a test signal is emitted via the transmitter of one measuring chain and is reflected on the boundary surface. The reflected portion is received by the receiver of the same measuring chain and is transmitted to the control and evaluation unit. The portion transmitted is received via the boundary surface of the receiver of the opposite measuring chain and is transmitted to the control and evaluation unit. The comparison of the two signals provides statements relating to the contamination of the boundary surfaces, the state of the area and the functioning of the measuring chains.

28 Claims, 6 Drawing Sheets

METHOD AND DEVICE FOR EVALUATING ELECTROMAGNETIC RADIATION

BACKGROUND OF THE INVENTION

The invention relates to a method of evaluating electromagnetic radiation which is utilized for representing at least one parameter of an area or region which is to be monitored. It also relates to a device for evaluating electromagnetic radiation utilized for representing at least one parameter of an area or region which is to be monitored, the device having a measuring head which is opreatively connected to a receiver and a transmitter, wherein the measuring head forms a boundary surface for the area or region to be monitored.

Electromagnetic radiation is evaluated in all areas of technology in the most varied functional connections. However, in this context reference is only made by way of example to control technology, e.g. in the form of light barriers, measurement and analysis technology, e.g. in the form of optically spectroscopic methods and not least safety and monitoring technology, e.g. for monitoring multiple-phase flows to avoid operational malfunctions as a consequence of obstructions, but also as a consequence of flying sparks or a developing seat of a fire. Particularly in relation to applications which are intended to provide warnings about dangerous operational states, there is a greater need to monitor the systems installed for this purpose to ensure that they function in problem-free manner. To this end, various technologies techniques are also already known.

Light barriers typically consist on the one hand of a transmitting unit and on the other hand a receiving unit lying opposite thereto at a spaced interval, wherein the receiving unit is arranged for receiving an electromagnetic signal transmitted by the transmitting unit and wherein the interruption in reception in turn serves to trigger a signal, a switching procedure or the like. As an alternative, these light barriers are also known in the form, wherein a light signal which is continuously emitted by a transmitting unit is reflected on a mirror unit, wherein in turn a receiving unit is provided which receives the reflected signal. It is known to treat the problem of increasing attenuation which is associated with increasing contamination of the surface intended for coupling the signal in and out, by virtue of the fact that a reduction in the received signal level below a specified value is interpreted as the beginning of an operational malfunction, and furthermore before there is a complete failure of the light barrier. In this case, there is no function-monitoring of the evaluation circuits within the transmitting and receiving unit used, so that malfunctions, e.g. cable fracture or the like are not readily identifiable in this area.

Electromagnetic radiation is utilized in a very broad spectral range and moreover is always tailored to suit the specific application, wherein insignificant spectral portions of radiation are generally blanked out. From the Applicant's brochure "Überwachungsanlage für MDF-Zyklon ABC 7" [monitoring system for MDF-cyclone ABC 7], it is known in the case of a cyclone separator used for the purpose of switching off the solids, in particular fibrous substances, to monitor the formation of a material build-up in the outlet region by installing a transmitting unit and a receiving unit which lie diametrically opposite one another in the walls of the separator and which are arranged to transmit and receive infrared radiation respectively, wherein the signal level is able to indicate the instantaneous solids charge of the flow within the separator and where an obstruction is beginning to form the pneumatic conveyance can be automatically switched off.

Another brochure by the Applicant entitled "Funkenlöschanlagen Sicherheit für Ihre Produktion" [spark extinguishment systems; safety for your production] discloses so-called spark detectors which can used for monitoring flying sparks in pneumatic conveyance systems. The spectral sensitivity of these detectors is tailored to the recognition of sparks or other dangerous elements which are inflammable, e.g. smolder spots, and are each formed by receiving units which are disposed in such a manner as to lie diametrically opposite each other in relation to the pipe line which is to be monitored. In order to test the smooth operation of the evaluation circuits, a test diode is also provided which emits a test signal which is identified and interpreted by the receiving unit. This function test which can be performed manually or in an automated manner according to e.g. specifiable time intervals or can even be performed automatically in an event-controlled manner renders it possible reliably to examine the spark detector for any internal malfunctions or damage, i.e. within the evaluation circuits. In the case of spark detectors of this type, it is also known to provide an external test probe in the pipe line in order to check for any possible contamination of the areas intended for coupling in the radiation which is to be received, said test probe lying opposite e.g. the spark detector to be examined and serving to generate a test signal, the reception quality of which renders it possible to derive information relating to the level of contamination. However, on the one hand this necessitates the provision of an aperture for assembly of the test probe and is thus characterized by an increased installation outlay. In addition, there is the problem that in general the test probe will also be subjected to the same conditions of contamination as the spark detector itself which is to be examined, so that in spite of the increased outlay, it is not reliably possible to rule out malfunctions as a result of contamination.

Finally, German patent publication DE 195 31 917 C1 discloses a detector for electromagnetic radiation which is designed as a flame detector for the purpose of monitoring areas or industrial processes, wherein both a receiver and also a transmitter are disposed within a housing with a window which is intended for coupling-in radiation to be received, wherein radiation emanating from the transmitter is reflected on the inner side of the window surface and wherein the contamination of the outer side of the window can be detected with the aid of the reflection characteristics thereof, so that the monitoring procedure is performed by the evaluation of the reflected signal. Although this device is able to establish that the outer side of the window has been contaminated, the evaluation circuits or the device are not examined as well.

The mode of operation of a device which is used to monitor a pipe line for pneumatic conveyance can be impaired by an accumulation of material within the pipe line, by contamination of the surface intended for coupling-in the radiation and by defects in electrical evaluation circuits. Using these known devices it is not possible to counteract these possible sources of disruption completely.

Against this background, it is the object of the invention to provide a method of the type mentioned in the introduction where possible without any additional installation outlay such that possible external and internal sources of disruption, which impair the working result, can be identified in a problem-free manner and in particular can be localized. In the case of a method of the generic type, this object is achieved by using a second measuring head disposed opposite to a first measuring head.

Accordingly, it is essential to the invention that the area to be monitored is allocated at least two measuring heads in a mutually opposite-lying arrangement, each one of said measuring heads being arranged for the purpose of coupling radiation in and out. The measuring heads can thus be configured completely identical to each other. With respect to their spectral sensitivity, they are preferably arranged in such a manner that the radiation received is merely that which corresponds to the parameter of the area to be monitored. By way of example only and without limitation, it is possible to mention the procedure of monitoring the area for the occurrence of heat sources, e.g. sparks, so that a considerable safety risk can depend upon the smooth execution of the method. It is then essential to the invention that function-testing is performed with the proviso that the transmitter of one measuring chain emits a defined test signal, e.g. a test pulse which is reflected in part on the boundary surface for the area to be monitored, wherein this part is received by the receiver of the same measuring chain. A further part of the test signal passes through the boundary surface and crosses the area, which is to be monitored, up to the receiver of the opposite-lying measuring chain. Signals which describe the two said radiation portions are thus provided at the outputs of the two measuring chains, wherein on the basis of these two signal portions it is possible, e.g. by a comparison with reference signals to derive a statement relating to the current mode of function of the device. The reflected signal portion can be used for example to identify the level of contamination of the boundary surface, as its reflection behavior is changed in a characteristic manner precisely by this contamination. By means of the signal which passes through the boundary surface and is received by the receiver of the opposite-lying measuring head it is possible to identify and examine the state of the area as such in the same manner as the function of the measuring chain. If the device is used, for example, in the case of a pipe line used for the pneumatic transportation of solids, it is possible using the last-named signal portion to derive a statement relating to an unusual accumulation of material inside the pipe line. Conversely, in addition to providing indicators to the contamination of the boundary surface, it is also possible using the first signal portion to produce a statement relating to the function of the electronic devices which are intended for the evaluation of the received signal portion and for the generation of an electrical measurement value describing said signal portion. Therefore, as a departure from the prior art, it is not only possible in accordance with the invention to detect external contamination of a boundary surface but also at the same time to incorporate into this test the current state of the area including the opposite-lying measuring head. A test procedure of this type which is initiated by triggering a test pulse via the measuring head is consequently triggered in an identical manner via the transmitter of the second measuring head, so that at the end of one complete testing cycle, a statement is provided relating to the current state of the two measuring heads. As a further departure from the prior art set forth in the introduction, the omission of one particular test probe means that there is a reduced engagement into the walls of the area to be monitored and thus reduced installation outlay overall, as existing lines of the measuring heads are utilized for the transmission of control signals, e.g. for triggering a test pulse and for acknowledging received signals.

It is also the object of the invention to provide a device which is designed to perform the method and which in comparison with the prior art is characterized by a lower installation outlay and a greater degree of reliability in the detection of operational malfunctions of the device which are in the stages of development. In the case of this type of device, this object is achieved by each measuring chain including a measuring head, a transmitter and a receiver arranged to receive radiation emitted by the transmitter of an oppositely positioned measuring chain.

The essential components of the device consist of at least two measuring chains and a control and evaluation unit which is disposed at a regular spaced interval from said measuring chains. For their part, the measuring chains consist of a measuring head, which forms the boundary surface for the area to be monitored, a transmitter and a receiver and evaluation circuits which are disposed downstream thereof and which are intended and arranged on the one hand to generate a test signal and to emit it via the transmitter and on the other hand to receive radiation via the receiver and to convert it into an electrical measurement signal which describes this radiation. Each measuring chain is thus arranged on its end lying opposite the measuring head for bi-directional communication with the control and evaluation unit. The latter is intended to trigger the test procedure as such and in particular to subject the provided measuring chains consecutively to the inventive checking procedure set forth in the introduction, and to compare the respectively received electrical signals, which characterize a predetermined progression of a received test signal, with reference signals, wherein this comparison is used to derive a statement relating to the current state of the device. Furthermore, with the aid of the different radiation portions, which are received in each case as the system response, namely on the one hand the reflected radiation portion and on the other hand the radiation portion which has passed through the area up to the receiver of the opposite-lying measuring head, it is possible to derive differentiated statements relating to the type of possible malfunction.

In dependence upon the directional characteristic of the functional elements used for coupling the radiation in and out, the number of measuring chains connected within the framework of a device in accordance with the invention is governed by virtue of the fact that the area to be monitored is covered completely. If permitted by the directional characteristics, two measuring chains can be sufficient.

In the most convenient case, a transmitter and a receiver are located in each case in a closed housing which is separated from the area, which is to be monitored, by virtue of a window which acts in a sealing manner. However, it is also possible to form the boundary surface for the area, which is to be monitored, directly by the end side of an optical wave guide. The temperatures of the atmosphere prevailing within the area which is to be monitored determine whether the area contains mechanically or chemically aggressive substances.

In an advantageous manner, the optical wave guide is utilized bi-directionally, so that it is possible to couple radiation in and out over the same boundary surface for the area which is to be monitored. At the end remote from the area which is to be monitored, the optical wave guide end cooperates with a transmitter and a receiver which in this case are always disposed in pairs. This embodiment of the device has the particular advantage that the said boundary surface can be disposed at a spaced interval with respect to the functional elements, in which the coupled-in radiation is evaluated, so that the last-named location is not subjected to the possibly unfavourable thermal influences of the area which is to be monitored.

There are many ways of forming the measuring chain, in particular its functional elements which are utilized for the purpose of forming and evaluating the measurement value.

In accordance with one emboidment, it is provided that disposed between the window of the measuring head on the one hand and a receiver/transmitter pair is an element of an optical wave guide which thus forms part of the signal transmission path.

In accordance with another embodiment, it is provided that all of the elements of a measuring chain can be disposed within a single housing which thus forms a constructional unit which is arranged to receive a signal, which triggers a testing procedure, or is arranged for the transmission of an electrical signal which describes a received radiation portion. The comparison with a reference signal can be performed in the measuring head itself and only the result can be relayed to a control and evaluation unit. In the latter case, the control and evaluation unit assumes only the synchronization of the transmission and reception processes. The spatial distribution of the elements of a measuring chain can thus be selected according to considerations of expediency. In particular, the control and evaluation unit can also be integrated into the measuring chain and disposed together with this in a common housing.

A further embodiment is directed to variations in the practical formation of the connection between a control and evaluation unit on the one hand and the measuring chains on the other hand. Generally, the control and evaluation unit is disposed some distance apart from the measuring chains which is particularly advantageous in the case of relatively large installations. The connection can be formed by cable but also by optical wave guides, in particular flexible optical wave guides—however, it is also possible to consider a radio path.

It is particularly expedient if the control and evaluation unit is provided with an external interface which is intended to establish a connection with a higher-ranking control system. For example, this can be the control system of the installation which incorporates the area which is to be monitored, since it is also possible in this manner to assist in achieving a meaningful test result. Therefore, it is possible to tailor the test procedure to suit the process being performed in the installation, so that, for example, test procedures are not performed if there is already a substantial material loading in the said area, in order to prevent a corresponding contamination from being signaled in error as a result of substantial attenuation of the received signal.

BRIEF DESCRIPTION OF THE DRAWINGS

The invention will be explained in detail hereinunder with reference to the embodiments which are illustrated schematically in the drawings, in which.

DETAILED DESCRIPTION OF PREFERRED EMBODIMENTS

Figure 1:
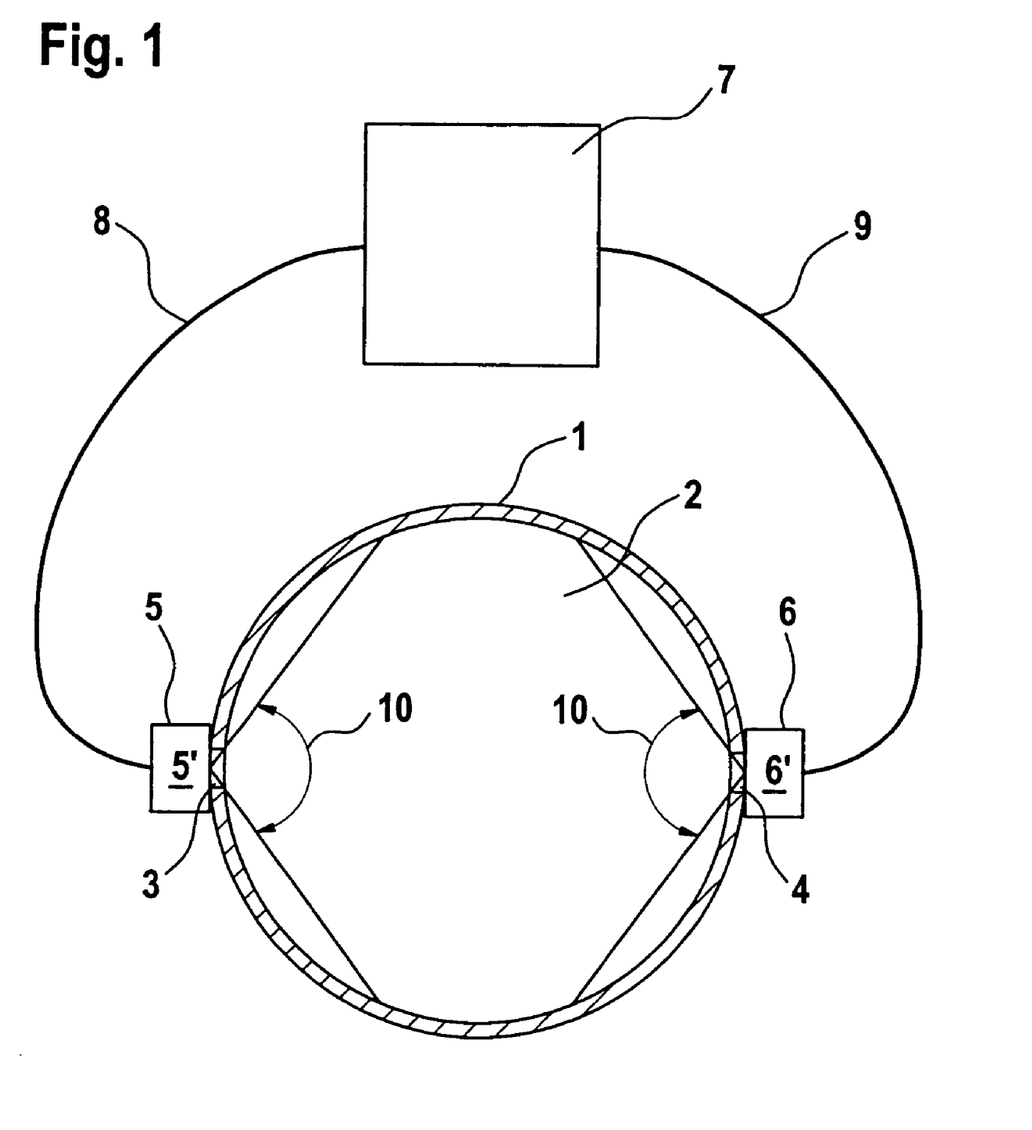
FIG. 1 shows a first embodiment of the invention in an application in a pipe line for the pneumatic conveyance of substances.

In FIG. 1, the reference numeral 1 designates a pipe line which is intended for the pneumatic conveyance of granular or fibrous materials and whose interior space forms the area 2 which is to be monitored for the occurrence of dangerous operational states, in this case monitoring for the occurrence of sparks or other dangerous elements which are inflammable, such as e.g. smolder spots within the material flow which moves perpendicular with respect to the plane of the drawing in FIG. 1.

For this purpose, the pipe line is provided on two diametrically opposed sides with apertures 3, 4 which cooperate with housings 5, 6 which are attached to the pipe line 1. In a manner to be explained in detail hereinunder, the housings 5, 6 include all of the elements of a measuring chain which consist of a measuring head which protrudes into the respective bore 3, 4 and forms a boundary surface for the area 2, of a transmitter and a receiver whose spectral sensitivity is limited to the detection of the sparks entrained in the material flow or to the detection of other dangerous elements which are inflammable such as e.g. smolder spots, and said elements of the measuring chain consist of functional elements whose purpose is to convert radiation, which is coupled in via the receiver, into a corresponding electrical signal, or to convert an incoming electrical signal via the transmitter into radiation according to a defined signal form. The constructional units which are combined in this manner in the housings 5, 6 are connected on the output-side via cables 8, 9 to a remotely disposed control and evaluation unit 7. The mutually opposite measuring heads each comprise approximately the same aperture angles of e.g. ca. 110°, so that the entire area 2 can be covered completely.

In order to test the functional reliability of the device illustrated, a function test of the left-hand side constructional unit 5' is first initiated via the control and evaluation unit 7 such that the transmitters of said constructional unit emit a test signal, e.g. a characteristic test pulse which is partially reflected on the boundary surface for the area 2 and passes partially through this boundary surface. This division is influenced quantitatively mainly by the external contamination of the said boundary surface. The reflected radiation portion is received by the receiver of the constructional unit 5' and the radiation portion which has issued out into the area 2 is received by the receiver of the opposite-lying constructional unit 6'. The radiation portions which are received by the two constructional units 5', 6' as a result of the test pulse are represented by corresponding electrical signals and are fed to the control and evaluation unit 7 for verification purposes, i.e. in particular for a comparison with reference signals. Therefore, by reason of a test pulse the contamination of the boundary surface, the state of the transmission path between the boundary surface and the transmitter or the receiver within the constructional unit 5' and the state of the external transmission path within the space 2 are subjected to a function-test. If the comparison with stored reference signals leads to the conclusion that there is a malfunction, the malfunction can be localized at its origin and can be signaled via a correspondingly triggered switching procedure. If the comparison with reference signals leads to the conclusion that there is no significant malfunction, the same procedure is repeated, in that now a test pulse is transmitted via the constructional unit 6', wherein in turn a reflected portion is detected via the receiver of the construction unit 6' and a portion, which has passed into the area 2, is detected via the receiver of the constructional unit 5' and wherein after conversion of the measurement value a comparison with reference signals is performed by means of the control and evaluation unit 7.

Since, in each case, the internal relationships of a constructional unit 5', 6', i.e. the functional capability of the measuring chains, which are installed in said constructional units, beginning with the boundary surface up to the output-side generation of an electrical signal representing the respective radiation portion, the contamination of the boundary surfaces to the area 2 and the state of the area 2 between the mutually opposite constructional units are subjected to testing, e.g. to test for the occurrence of an excessive accumulation of material, the functional reliability of the entire device with respect to internal and external sources of interference or defects is tested in a complete manner which is in contrast to the prior art set forth in the introduction.

In the following Figures of the drawings, functional elements which correspond to those in FIG. 1 are numbered accordingly.

Figure 2:
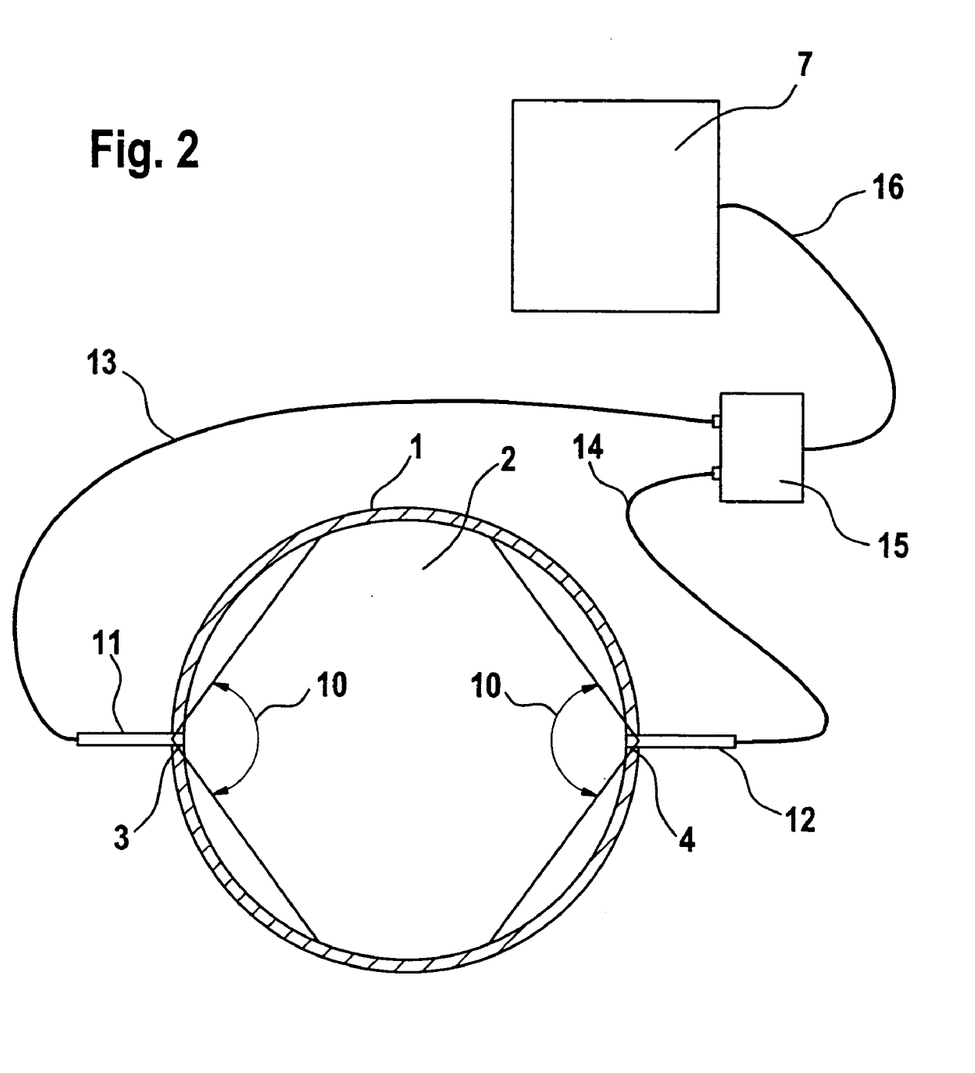
FIG. 2 shows a second exemplified embodiment of the invention in an application corresponding to FIG. 1.

An essential feature of the exemplified embodiment illustrated in FIG. 2 is a different design of the respective measuring chains, in particular the spatial distribution of their individual components. The boundary surface for the area 2 of each measuring chain is thus formed by the end-side end of an optical wave guide rod 11, 12 which is inserted in the respective aperture 3, 4 and which is connected to a constructional unit 15 in each case via an optical wave guide 13, 14. The precise structure of the constructional unit 15 will be explained in detail hereinunder. It is essential in this respect that each of the two optical wave guides 13, 14 within the constructional unit 15 is operatively connected to a transmitter and a receiver, so that each of the two optical wave guides is arranged for the transmission of a light signal in the direction towards the optical wave guide rod 11 and for receiving a light signal from said optical wave guide rod. For its part, the constructional unit 15 is connected via a cable 16 to the control and evaluation unit 7.

In this respect, it is essential that the constructional unit 15 is arranged for the output-side generation of an electrical signal which is to be transmitted via the line 16 and which describes a received radiation portion and does this to such an extent that a test pulse can be transmitted in the direction towards the respective optical wave guide rod 11, 12 via each one of the transmitters allocated in each case to an optical wave guide 13, 14.

The basic mode of operation corresponds to that of the exemplified embodiment shown in FIG. 1. By actuating the constructional unit 15, the control and evaluation unit 7 serves to transmit a defined test signal initially via one of the two optical wave guides 13, 14, which test signal is partially reflected on the boundary surface of the respective optical wave guide rod 11, 12 to the area 2 and issues out in part into the area 2 and is received by the respectively opposite-lying optical wave guide rod. The test pulse thus triggers response signals which correspond to two signal portions, namely a reflected portion and a portion transmitted over the area 2, wherein both radiation portions are received via the two receivers of the constructional unit 15 and, after conversion of the measurement value, are transmitted via the cable 16 as an electrical signal to the control and evaluation unit 7 for evaluation purposes. The two radiation portions are evaluated according to the preceding exemplified embodiment of FIG. 1.

The entire testing cycle which, corresponding to two optical wave guide rods 11, 12, consists of two phases is performed consecutively in the two optical wave guide rods 11, 12 and can be triggered automatically via the control and evaluation unit 7.

Figure 3:
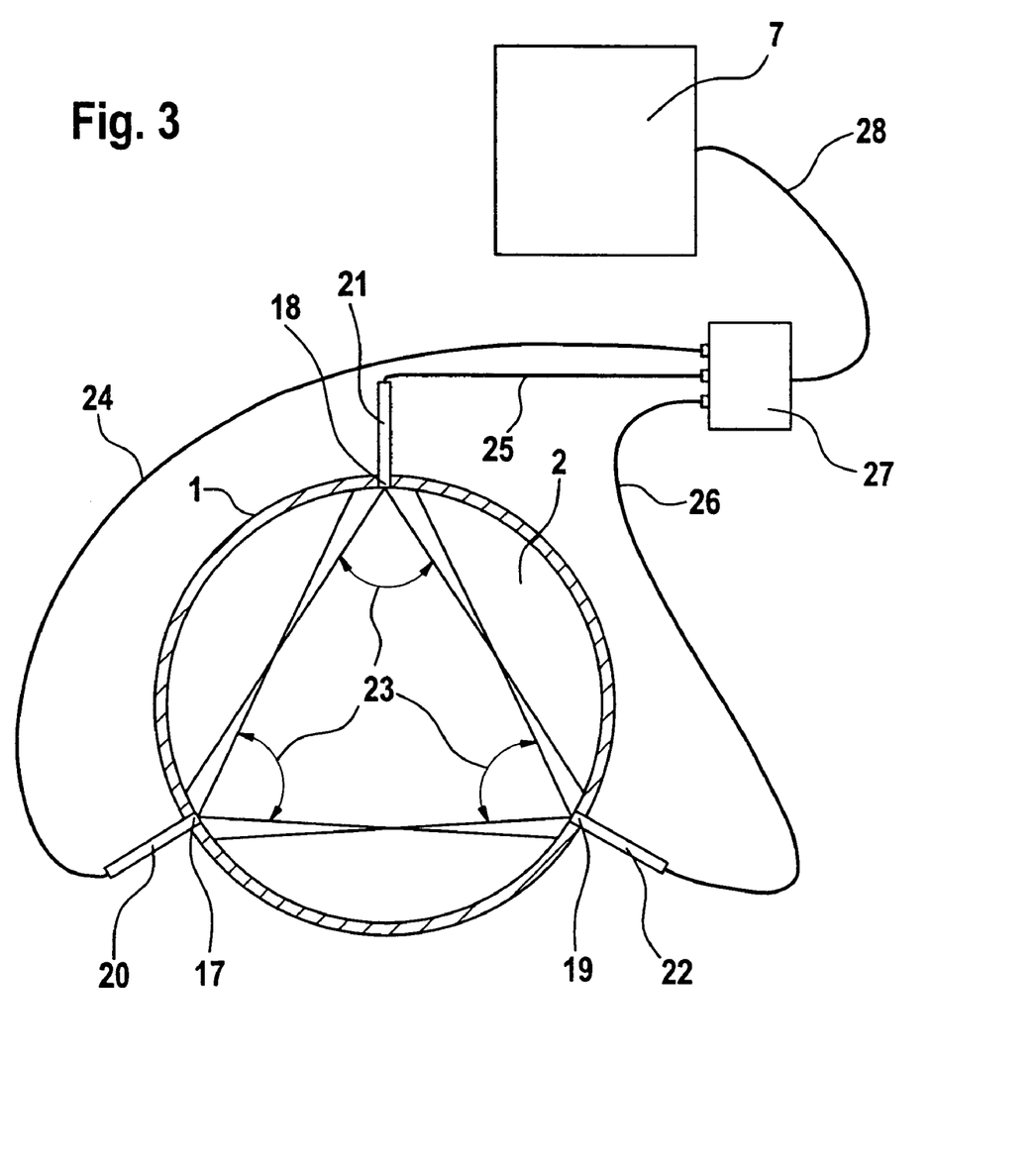
FIG. 3 shows a further exemplified embodiment of the invention in an application corresponding to the preceding Figures of the drawing.

In the case of the above-described exemplified embodiment as shown in FIG. 2, it has been assumed that the aperture angle 10 of the two optical wave guide rods is sized in such a manner as to enable the area 12 to be covered completely. In general, this will require, for example, the surface to be worked into a spherical shape accordingly, in order to achieve this aperture angle. In the case of the exemplified embodiment as shown in FIG. 3, the cross-section of the pipe line 1 is provided correspondingly with three apertures 17, 18, 19 which are distributed uniformly in the circumferential direction and into which an optical wave guide rod 20, 21, 22 is inserted in each case. The number of optical wave guide rods 20 to 22 utilized is selected in dependence upon their aperture angles 23 which in the configuration shown amounts to about 70°, and furthermore with the objective of ensuring complete coverage of the area 2.

Each one of the optical wave guide rods 20 to 22 is connected via an optical wave guide 24, 25, 26 to a constructional unit 27, whose basic structure corresponds to the constructional unit 15 as shown in FIG. 2, with the only different being that in this case three optical wave guides instead of two are connected on the input-side. The constructional unit 27 is connected in turn on the output-side via a cable 28 to the control and evaluation unit 7.

As in the case of the above-described exemplified embodiments of FIGS. 1 and 2, a procedure to test the functional reliability is triggered via the control and evaluation unit 7 by virtue of the fact that a defined test signal is transmitted via the transmitter of the optical wave guide 24 to the optical wave guide rod 20, which test signal is partially reflected on the boundary surface for the area 2 and is transmitted via the optical wave guide 24 to the receiver allocated thereto inside the constructional unit 27. A further portion which passes through the boundary surface of the optical wave guide rod 20 and issues out into the area 2 is coupled in via the boundary surfaces of the two other optical wave guide rods 21, 22 and is transmitted to the receivers which are allocated respectively thereto inside the constructional unit 27. As a result, three measurement values are thus provided which correspond to received radiation signals and signal forms respectively and which, after conversion into corresponding electrical signals, are transmitted via the cable 28 to the control and evaluation unit 7 for evaluation purposes. As a result, this test procedure is repeated cyclically via the optical wave guide rods 21, 22, so that corresponding to the three inserted optical wave guide rods 20 to 22, a complete testing cycle comprises three partial procedures. If one of the partial procedures leads a malfunction being signaled, be it as a result of contamination of the boundary surface or as a result of an unusual accumulation of material inside the area 2, which serves correspondingly to attenuate a signal which is to be transmitted through the area 2, a corresponding malfunction warning is signaled via the control and evaluation unit 7.

Figure 4:
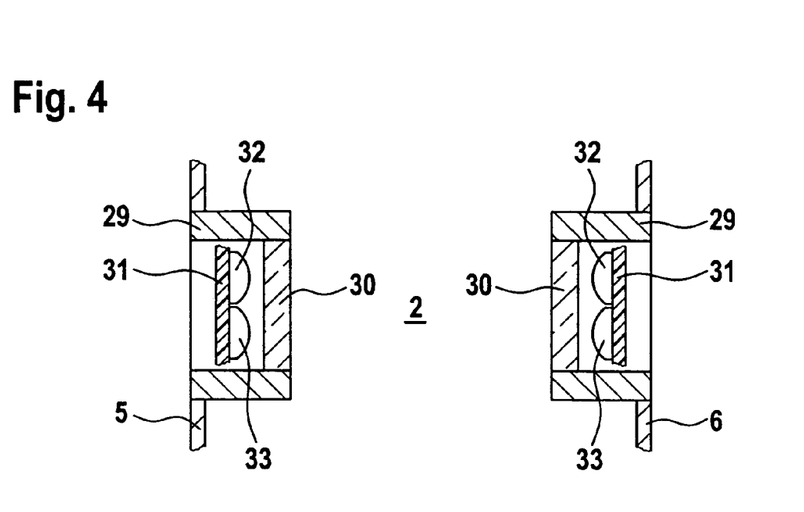
FIG. 4 shows a partial illustration in cross-section of a first embodiment of measuring heads in accordance with the invention.

FIG. 4 illustrates a specific design of the parts, which are arranged for transmission and reception, of the housings 5, 6 or constructional units 5', 6' used for example in the device as shown in FIG. 1. As shown in this case, the housings 5, 6 are provided with an e.g. tubular element-like attachment 29 which is inserted into an aperture in a housing wall and into whose front-side end face, i.e. facing the area 2, a radiation-transparent cover 30, e.g. a glass or synthetic material disk, is inserted in a sealing manner. The attachment 29 can be inserted in each case into the aperture 3, 4 in the wall of the pipe line 1.

The reference numeral 31 designates in each case a carrier board or a printed circuit board, on which are disposed inter alia a transmitter 32 and a receiver 33. In practice, these functional elements can be a transmitting diode and a receiving diode, whose spectral sensitivity is limited according in this case to the detection of sparks or other dangerous elements which are inflammable, e.g. smolder spots. Not illustrated in the drawing are other functional elements which are disposed on the respective printed circuit board and are intended for the supply of energy, the control and in particular the conversion of the measurement value of the signal portions which are coupled out and in respectively via the transmitter and the receiver. It is essential that the transmitter 32 and the receiver 33 are disposed closely adjacent to each other and disposed at a small spaced interval directly opposite the inner side of the radiation-transparent cover 30. In this case, the outer side of the cover 30 forms the boundary surface for the area 2, through which the material flow to be monitored for flying sparks or for other dangerous, inflammable elements moves.

Figure 5:
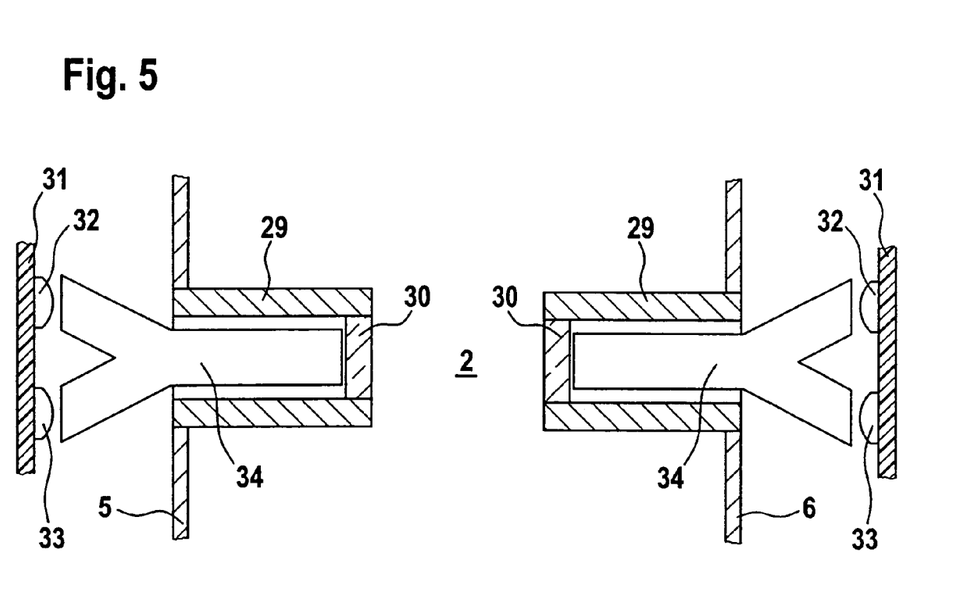
FIG. 5 shows a partial illustration in cross-section of a second embodiment of measuring heads in accordance with the invention.
Figure 6:
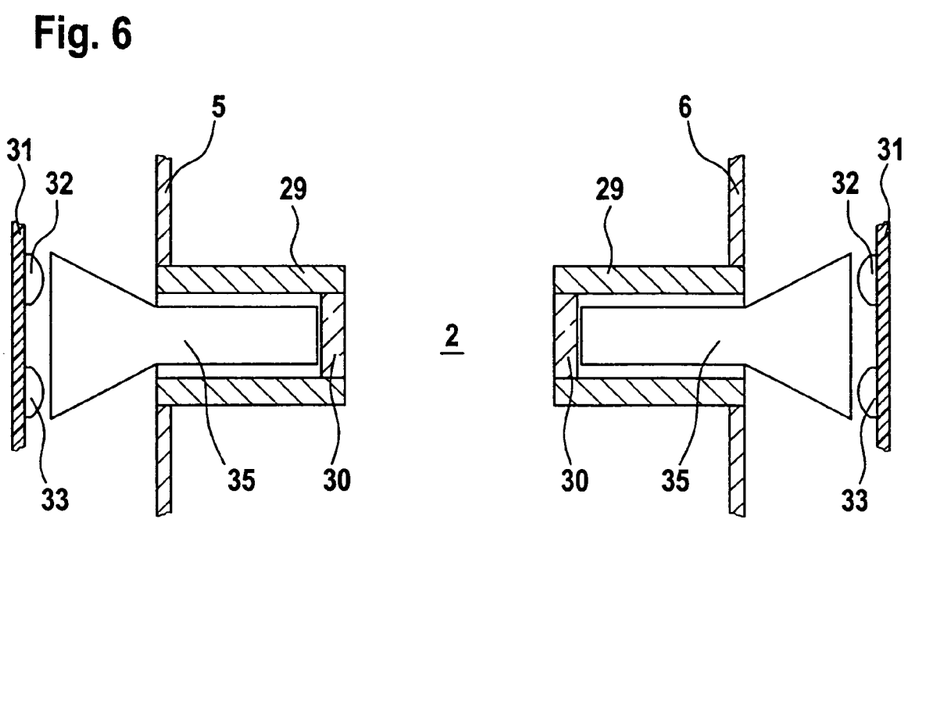
FIG. 6 shows a partial illustration in cross-section of a third embodiment of measuring heads in accordance with the invention.

The transmitter 32 and the receiver 33 can be coupled to the radiation-transparent cover 30 in different ways, including those in FIGS. 5, 6 to be described hereinunder which, without claiming to be complete, are to be considered merely as possible variations of the illustration as shown in FIG. 4.

Located between the radiation-transparent cover 30 on the one hand and the transmitters 32 or receivers 33, is an optical wave guide rod 34, 35 as shown in FIGS. 5 and 6, which is configured with the proviso that its portion which extends within a tubular element-like attachment 29 is arranged both for transmitting and also receiving signals, so that outside the attachment, a branch, as shown in FIG. 5, or merely an extension of the cross-section, as shown in FIG. 6, is connected to this portion, and furthermore with the proviso that the transmitter 32 and the receiver 33 are able to interact with the optical wave guide rod 34. Optical wave guide elements with the same degree of flexibility can be connected to the optical wave guide rod 34, a consideration which is of particular interest if relatively high temperatures are expected to prevail within the area 2 and the carrier board 31 must be disposed together with all of the electronic devices, which are installed on said board, in such a manner as to be protected against the effects of excessive heat. In contrast to the embodiment as shown in FIG. 4, these variations offer the advantage that the transmitter and the receiver can be accommodated spaced further apart from each other on the board. Furthermore, an aperture, into which the attachment 29 is to be inserted, can be formed correspondingly smaller.

Figure 7:
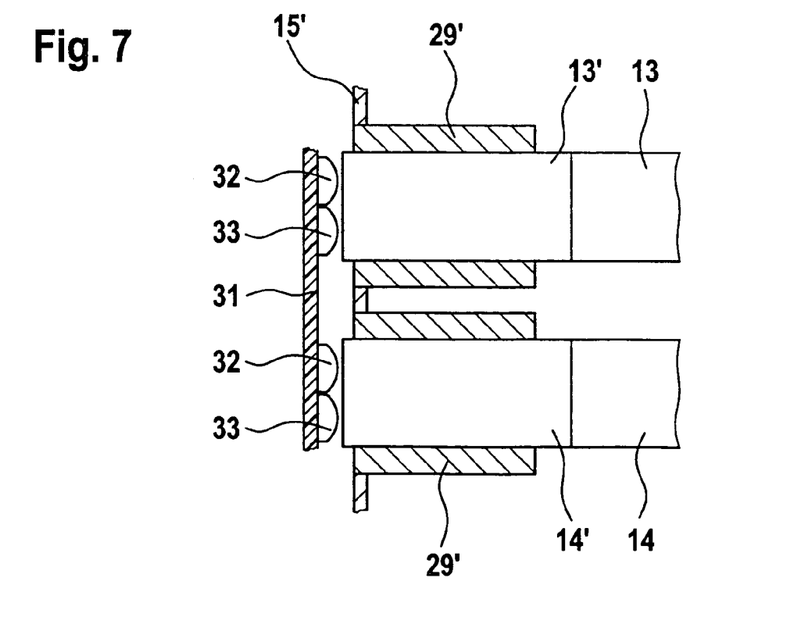
FIG. 7 shows a partial illustration in cross-section of a further embodiment of a measuring head in accordance with the invention.

The exemplified embodiment as shown in FIG. 7 can be used for the constructional units 15, 27 according to FIGS. 2 and 3. In this case, the ends 13', 14' of the optical wave guides 13, 14 are inserted into cylindrical attachments 29' which for their part are inserted into apertures in the wall 15' e.g. of the constructional unit 15. The end sides of the optical wave guide ends 13', 14' lie directly opposite the transmitters 32 and receivers 33 which are disposed in pairs on the printed circuit board 31, so that each of the two optical wave guides 13, 14 is able to interact with a transmitter/receiver pair allocated thereto, corresponding to the mode of operation illustrated in FIG. 2. In the nature of things, the same principle can also be applied to the exemplified embodiment described with respect to FIG. 3, with the only difference being that now three pairs of transmitters and receivers are disposed lying opposite in each case to three optical wave guide ends.

In the case of the variation shown in FIG. 7, it is also possible in essence to provide a branch arrangement with the inter-positioning of rigid optical wave guide rods as in the case of FIG. 6, e.g. in order to adapt to the transmitters and receivers which are spaced apart from each other in the surface of the printed circuit board.

Figure 8:
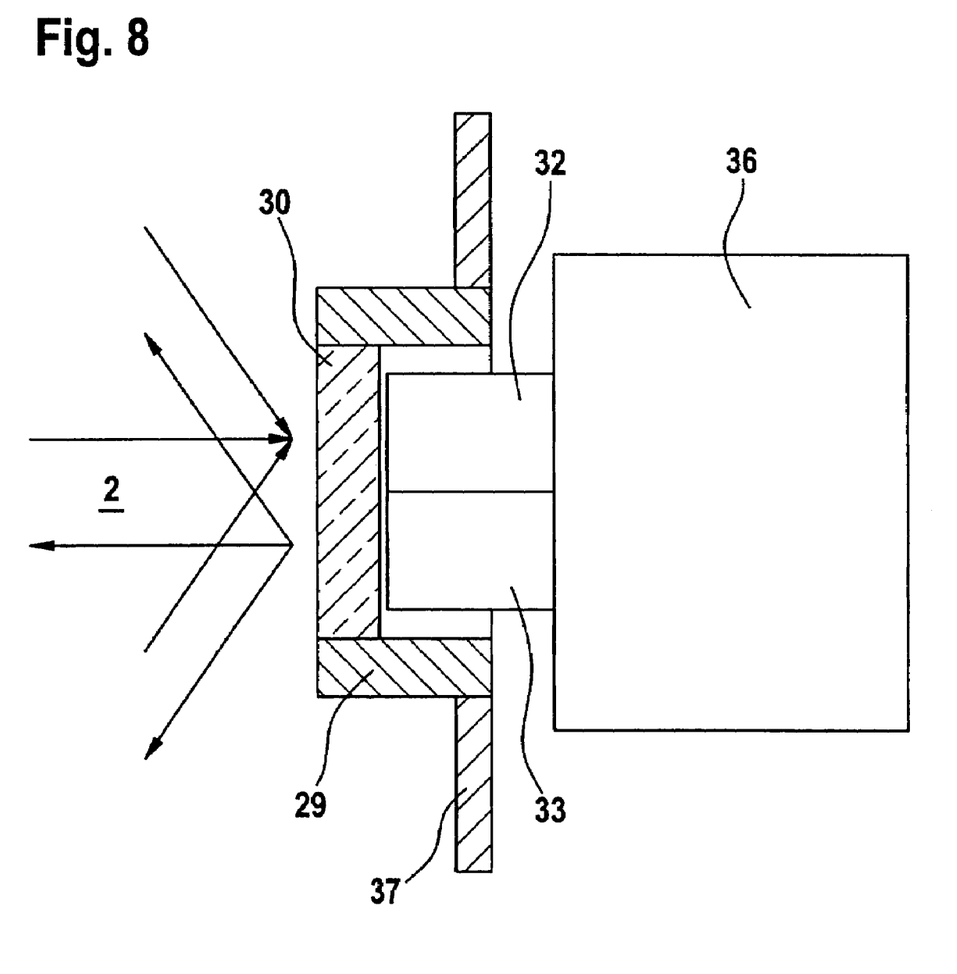
FIG. 8 shows a further illustration in cross-section of a measuring head in accordance with the invention.

In the case of the exemplified embodiments illustrated above, it is always assumed that the control and evaluation unit 7 is disposed spatially separated from the constructional units 5', 6', 15 which contain the components of the respective measuring chain—these are the elements which are disposed functionally between the interface to the area 2 and the elements which are intended for the output-side generation of electrical signals which can be processed and which describe received radiation, and for the transmission of a control signal for the purpose of generating a defined test pulse. In contrast to this, the embodiment as shown in FIG. 8 includes a control and evaluation unit 36 which is combined with the said elements of the measuring chain spatially in close proximity, i.e. in a single housing. In turn, the reference numeral 32 designates a transmitter and the reference numeral 33 designates a receiver which are disposed on the end-side directly adjacent to the radiation-transparent cover 30 which is intended for coupling radiation in and out. All of the components are combined in one housing 37 which comprises an external interface which in conjunction with a higher-ranking control system serves to trigger a test procedure. In relation to an embodiment of the device according to the invention as shown in FIG. 1, a constructional unit which is accommodated in a housing 37 can replace each of the constructional units 5' 6' disposed therein, so as to achieve a reduced installation outlay overall.

Irrespective of the spatial arrangement, as shown in FIG. 8, of the devices required for producing the control and evaluation unit, this control and evaluation unit is advantageously always provided with an external interface for connection to a higher-ranking control system, so that the test procedures which are to be carried out can be adapted to the process which incorporates the material flow within the pipe line 1, in order e.g. to prevent a test from being carried out at times when there is a high material density contained within the line.

The invention claimed is:

1. A method of testing functionality of an apparatus for monitoring a region bounded by a surface, said apparatus monitoring said region by evaluating electromagnetic radiation transmitted into said region, said testing method comprising the steps of:
  providing a first electromagnetic radiation transmitter adapted to transmit radiation into said region;
  providing a first electromagnetic radiation receiver adapted to receive radiation within said region;
  providing a second electromagnetic radiation receiver adapted to receive radiation within said region;
  transmitting electromagnetic radiation into said region using said first transmitter;

receiving, with said first receiver, said electromagnetic radiation from said first transmitter, as reflected from said surface;

receiving, with said second receiver, said electromagnetic radiation directly from said first transmitter;

using said radiation received by both said first and second receivers as a signal indicative of the functionality of said apparatus.

2. An apparatus for monitoring a region bounded by a surface according to claim 1, said apparatus comprising:
a control and evaluation unit;
a first measuring head in communication with said evaluation unit, said first measuring head including said first electromagnetic radiation transmitter and said first electromagnetic radiation receiver adapted to transmit and receive electromagnetic radiation in said region;
a second measuring head in communication with said evaluation unit, said second measuring head including a second electromagnetic radiation transmitter and said second electromagnetic radiation receiver adapted to transmit and receive electromagnetic radiation in said region; and
wherein said apparatus has a functional test mode wherein radiation emitted by one of said transmitters in one of said measuring heads is received directly by said receiver in the other of said measuring heads and by reflection from said surface in said receiver in said one measuring head, each of said receivers being adapted to generate a signal and send said signal to said control and evaluation unit for evaluation of the functionality of said apparatus.

3. Apparatus according to claim 2, wherein said measuring heads are positioned in spaced relation relative to one another so as to view said region completely.

4. Apparatus according to claim 3, further comprising an optical waveguide positioned between said region and one of said measuring heads for transmitting electromagnetic radiation between said region and said transmitter and said receiver associated with said one measuring head.

5. Apparatus according to claim 3, further comprising a cable adapted to establish said communication between said control and evaluation unit and one of said measuring heads.

6. Apparatus according to claim 3, further comprising radio means for establishing said communication between said control and evaluation unit and one of said measuring heads.

7. Apparatus according to claim 3, further comprising a control system and an interface connecting said control system to said control and evaluation unit.

8. Apparatus according to claim 3, wherein at least one of said measuring heads comprises:
a housing containing one of said transmitters and said receivers; and
a window positioned in said housing, said window forming a portion of said surface bounding said region.

9. Apparatus according to claim 8, further comprising an optical waveguide positioned within said housing between said window and said transmitter and said receiver for transmitting electromagnetic radiation between said window and said transmitter and said receiver.

10. Apparatus according to claim 8, wherein said one measuring head mounted within said housing forms a self-contained unit for receiving and transmitting said electromagnetic radiation for said functional test mode and for monitoring said region.

11. Apparatus according to claim 8, wherein said control and evaluation unit is located within a single housing.

12. Apparatus according to claim 8, further comprising a cable adapted to establish said communication between said control and evaluation unit and one of said measuring heads.

13. Apparatus according to claim 8, further comprising radio means for establishing said communication between said control and evaluation unit and one of said measuring heads.

14. Apparatus according to claim 2, further comprising an optical waveguide having an end that forms a portion of said surface bounding said region, said optical waveguide being adapted to transmit electromagnetic radiation to and from said region.

15. Apparatus according to claim 14, wherein said optical waveguide is operatively connected to one of said receivers for transmitting said electromagnetic radiation from said region to said one receiver, said optical waveguide also being connected to one of said transmitters for transmitting said electromagnetic radiation from said one transmitter into said region.

16. Apparatus according to claim 14, wherein at least one of said measuring heads is mounted within a housing thereby forming a self-contained unit for receiving and transmitting said electromagnetic radiation for said functional test mode and for monitoring said region.

17. Apparatus according to claim 14, wherein said control and evaluation unit is located within a single housing.

18. Apparatus according to claim 14, further comprising a cable adapted to establish said communication between said control and evaluation unit and one of said measuring heads.

19. Apparatus according to claim 14, further comprising radio means for establishing said communication between said control and evaluation unit and one of said measuring heads.

20. Apparatus according to claim 2, wherein said first and second measuring heads are positioned in a single housing, said first and second measuring heads being connected to respective first and second optical waveguides, said waveguides being adapted to transmit electromagnetic radiation to and from said region, each of said optical waveguides having an end forming a portion of said surface bounding said region.

21. Apparatus according to claim 2, further comprising an optical waveguide positioned between said region and one of said measuring heads for transmitting electromagnetic radiation between said region and said transmitter and said receiver associated with said one measuring head.

22. Apparatus according to claim 2, wherein at least one of said measuring heads is mounted within a housing thereby forming a self-contained unit for receiving and transmitting said electromagnetic radiation for said functional test mode and for monitoring said region.

23. Apparatus according to claim 2, wherein said control and evaluation unit is located within a single housing.

24. Apparatus according to claim 2, further comprising a cable adapted to establish said communication between said control and evaluation unit and one of said measuring heads.

25. Apparatus according to claim 2, further comprising radio means for establishing said communication between said control and evaluation unit and one of said measuring heads.

26. Apparatus according to claim 2, further comprising a control system and an interface connecting said control system to said control and evaluation unit.

27. A method according to claim 1, further comprising the steps of:

providing a second electromagnetic radiation transmitter adapted to transmit radiation into said region;

transmitting electromagnetic radiation into said region using said second transmitter;

receiving, with said second receiver, said electromagnetic radiation from said second transmitter, as reflected from said surface;

receiving, with said first receiver, said electromagnetic radiation directly from said second transmitter; and using said radiation received by both said first and second receivers as another signal indicative of the functionality of said apparatus.

28. An apparatus for monitoring a region bounded by a surface, said apparatus monitoring said region by evaluating electromagnetic radiation transmitted into said region, said apparatus comprising:

a control and evaluation unit;

a first measuring head in communication with said evaluation unit, said first measuring head including an electromagnetic radiation transmitter and a first electromagnetic radiation receiver, said transmitter and first receiver being adapted, respectively, to transmit and receive electromagnetic radiation in said region;

a second measuring head in communication with said evaluation unit, said second measuring head including a second electromagnetic radiation receiver adapted to receive electromagnetic radiation in said region; and wherein said apparatus has a functional test mode wherein radiation emitted by said transmitter is received directly by said second receiver and by reflection from said surface in said first receiver, each of said receivers being adapted to generate a signal and send said signal to said control and evaluation unit for evaluation of the functionality of said apparatus.

* * * * *